United States Patent [19]
Goswani

[11] Patent Number: 5,993,738
[45] Date of Patent: Nov. 30, 1999

[54] ELECTROSTATIC PHOTOCATALYTIC AIR DISINFECTION

[75] Inventor: D. Yogi Goswani, Gainesville, Fla.

[73] Assignee: Universal Air Technology, Lake Hopatcong, N.J.

[21] Appl. No.: 09/078,286

[22] Filed: May 13, 1998

Related U.S. Application Data

[60] Provisional application No. 60/046,296, May 13, 1997.

[51] Int. Cl.$^6$ ................................. A61L 9/18; B03C 3/38
[52] U.S. Cl. .................................. 422/22; 422/4; 422/24; 422/121; 422/122; 96/16; 96/69; 96/98
[58] Field of Search .............................. 422/4, 5, 22, 24, 422/121, 122; 96/16, 69, 98

[56] References Cited

U.S. PATENT DOCUMENTS

| | | |
|---|---|---|
| 2,265,252 | 12/1941 | Shaefer . |
| 2,628,083 | 2/1953 | Rense . |
| 2,638,644 | 5/1953 | Rauhut . |

(List continued on next page.)

FOREIGN PATENT DOCUMENTS

| | | | |
|---|---|---|---|
| 76028/87 | 1/1988 | Australia . | |
| 63-80833 | 4/1988 | Japan . | |
| 1-234729 | 9/1989 | Japan . | |
| 2-207824 | 8/1990 | Japan . | |
| 3-106420 | 5/1991 | Japan . | |
| 2229365 | 9/1990 | United Kingdom | 422/121 |
| 94/11092 | 5/1994 | WIPO . | |

OTHER PUBLICATIONS

Matthews, *Solar Energy*, 38(6), 405–13 (1987).
Trivedi, *Photocatalytic Disinfection of Airbourne Microorganisms* (Univ. of Florida, Sep. 6, 1994).
Sabate et al., *J. Catal.*, 127, 167–77 (1991).
Suzuki, "Photocatalytic Air Purification on TiO$_2$ Coated Honeycomb Support," *Photocat, Purification and Treat. of Water and Air* (Ollis and Al–Ekabi, Eds., Elsevier Sci. Pubs. 1993) 421–434.
Fujishama et al., "Biochemical Application of TiO$^2$ Photocatalysts,"0 *Photocat. Purification and Treat. of Water and Air* (Ollis and Al–Ekabi, Eds., Elsevier Sci. Pubs. 1993) 193–205.
Wang et al., "Control of VOC Emissions from Air–Stripping Towers: Development of Gas–Phase Photocatalytic Process," *Photocat. Purification and Treat. of Water and Air* (Ollis and Al–Ekabi, Eds., Elsevier Sci. Pubs. 1993) 733–739.
Anderson et al., "Photodegradation of trichloroethylene in the gas phase using TiO$_2$ porous ceramic membrane," *Photocat. Purification and Treat. of Water and Air* (Ollis and Al–Ekabi, Eds., Elsevier Sci. Pubs. 1993) 405–420.
Wang et al., "Gas Phase Photocatalytic Process for the Control of VOC Emissions from Air–Stripping Towers," *Proc.–Annu. Conf. Am. Water Works Assoc.*, 585–605 (1993).
Ireland et al., "Inactivation of *Escherica coli* by Titanium Dioxide Photocatalytic Oxidation," *Applied and Environmental Microbiology*, vol. 9, No. 5, pp. 1668–1670.

*Primary Examiner*—Elizabeth McKane
*Attorney, Agent, or Firm*—Lerner, David, Littenberg, Krumholz & Mentlik, LLP

[57] ABSTRACT

A method for disinfecting an airstream containing microorganisms by electrostatic precipitation by passing the airstream through the space between at least one grounded collection plate having at least one electrode spaced apart therefrom connected to a source of electrical potential, wherein the improvement comprises contacting the airstream with a photocatalyst having a predetermined band gap energy coated on the surface of each grounded collection plate and illuminated with photons having a wavelength corresponding to the band gap energy of the photocatalyst, so that at least a portion of the microorganisms that collect on the grounded collection plate are destroyed by photocatalytic oxidation. Devices embodying disinfecting methods are also disclosed.

22 Claims, 4 Drawing Sheets

U.S. PATENT DOCUMENTS

| | | | |
|---|---|---|---|
| 3,973,927 | 8/1976 | Furchner et al. | 422/22 X |
| 4,102,654 | 7/1978 | Pelling . | |
| 4,306,358 | 12/1981 | King, Jr. | 34/487 |
| 4,437,954 | 3/1984 | Sammells et al. | 422/186 X |
| 4,464,336 | 8/1984 | Hiramoto . | |
| 4,554,719 | 11/1985 | Lewis | 29/890.039 |
| 4,694,179 | 9/1987 | Lew et al. | 422/24 X |
| 4,734,111 | 3/1988 | Hoffmann et al. | 435/266 |
| 4,750,917 | 6/1988 | Fujii | 422/24 X |
| 4,806,768 | 2/1989 | Keutenedjian . | |
| 4,859,594 | 8/1989 | Portier | 435/172.1 |
| 4,892,712 | 1/1990 | Robertson et al. | 422/24 X |
| 4,931,654 | 6/1990 | Horng . | |
| 4,955,208 | 9/1990 | Kawashima et al. | 422/122 X |
| 4,966,759 | 10/1990 | Robertson et al. | 422/186 |
| 4,990,311 | 2/1991 | Hirai et al. | 422/4 |
| 5,032,241 | 7/1991 | Robertson et al. | 204/157.15 |
| 5,045,288 | 9/1991 | Raupp et al. | 422/186.3 |
| 5,069,885 | 12/1991 | Ritchie | 422/186 |
| 5,151,252 | 9/1992 | Mass | 422/24 X |
| 5,186,907 | 2/1993 | Yanagi et al. | 422/186.3 |
| 5,200,156 | 4/1993 | Wedekamp | 422/24 X |
| 5,219,534 | 6/1993 | Reynolds | 422/186.3 |
| 5,225,167 | 7/1993 | Wetzel | 422/121 |
| 5,227,053 | 7/1993 | Bryan | 210/143 |
| 5,260,036 | 11/1993 | Weigold et al. | 422/186.3 |
| 5,262,066 | 11/1993 | Van Soye et al. | 422/24 X |
| 5,397,552 | 3/1995 | Weigold et al. | 422/186.3 |
| 5,413,768 | 5/1995 | Stanley, Jr. | 422/24 X |
| 5,433,763 | 7/1995 | Shagott et al. | 55/323 |
| 5,449,443 | 9/1995 | Jacoby et al. | 204/157.3 |
| 5,456,740 | 10/1995 | Snow et al. | 96/11 |
| 5,501,801 | 3/1996 | Zhang et al. . | |
| 5,554,300 | 9/1996 | Butters et al. . | |
| 5,589,132 | 12/1996 | Zippel . | |
| 5,604,339 | 2/1997 | Tabatabaie-Raissi et al. . | |

ELECTROSTATIC PHOTOCATALYTIC AIR DISINFECTION

CROSS-REFERENCE TO RELATED APPLICATION

The present application claims benefit of U.S. Provisional Patent Application Ser. No. 60/046,296, filed on May 13, 1997, the disclosure of which is hereby incorporated by reference herein.

BACKGROUND OF THE INVENTION

The present invention relates to methods for disinfecting airstreams containing microorganisms by electrostatic precipitation. More particularly, the invention relates to methods in which at least one of the grounded collection plates of an electrostatic precipitator in contact with an airstream containing microorganisms is coated with a photocatalyst having a predetermined band gap energy and illuminated with photons having a wavelength corresponding to the band gap energy of the photocatalyst. The present invention also relates to electrostatic precipitators having collection plates coated with a photocatalyst having a predetermined band gap energy and a light source positioned to illuminate the photocatalyst coating with photons having a wavelength corresponding to the band gap energy of the photocatalyst.

Americans spend 90% of their time indoors, and while indoors, are exposed to a variety of airborne contaminants such as volatile organic compounds (VOC's), radon and biological organisms. In a 1980 study, the Environmental Protection Agency (EPA) concluded that indoor air pollution posed a greater health risk than outdoor air pollution. Indoor air contamination is estimated to cause significant increases in medical costs and a decline in worker productivity.

Pollutant levels from individual indoor sources may not pose a significant risk by themselves, however, many buildings have more than one source that contributes to indoor air pollution. Illnesses resulting from such indoor pollutants are sometimes known as the "sick building syndrome." Common causes of indoor air pollution are unwanted particulate matter, unwanted chemical substances, volatile organic compounds (VOC's) and microbial contaminants. In the first two cases, conventional technology can often ameliorate the contamination by filtration and adequate ventilation. The problem of volatile organic compounds and microbiological contamination creates a more serious obstacle, not easily solved by filtration or ventilation.

Because so many Americans spend a great deal of time in offices and buildings with various mechanical, heating, cooling, and ventilating systems, such systems pose a significant health risk of biological contamination. In recent years, biological problems in indoor environments have received considerable attention. The 1976 Legionnaires' disease outbreak in Philadelphia is probably the most publicized case of illness caused by indoor pollutants.

Biological contamination of building systems can include contamination by bacteria, molds, and viruses. There are a variety of places in a building's heating, mechanical, air-conditioning, refrigeration, and other air and water circulating systems that can become a breeding ground for biological contaminants. Moreover, the forced air of a building's heating, ventilation and air-conditioning systems can distribute the contaminants throughout the building, thus compounding the contamination.

UV disinfection has been widely used in the past to destroy biological contaminants and toxic chemicals. Such UV treatment has worked well for disinfection, but the indoor environment may also be contaminated with low level toxic chemicals such as formaldehyde, styrene, and toluene. Ultraviolet energy alone has proven ineffective in degrading these chemicals. For instance, U.S. Pat. No. 5,045,288 to Raupp and Dibble, and U.S. Pat. Nos. 4,892,712, 4,966,759 and 5,032,241 to Robertson and Henderson use UV to treat fluids and gases that contain pollutants.

An alternative that has gained much attention is photocatalytic oxidation, which involves the use of a photocatalyst such as $TiO_2$ for the total destruction of both hydrocarbons and microorganisms. Patela, *Antibacterial Effect Of Catalyzed Radiation*, Masters Thesis, University of Florida, Gainesville (1993), reports powdered $TiO_2$ to be capable of killing *Serratia marcescens* after irradiation for 60–120 minutes in water. Saito et al., *J. Photochem. Photobiol. B:Biol*., 14, 369–79 (1992); Matsunaga, *J. Antibact. Antifungic. Agents*, 13, 211–20 (1985); Nagane et al., *J. Dent. Res*., 68, 1696–7 (1989) and Moriaka et al, *Caries. Res*., 22, 230–1 (1988), report $TiO_2$ to be capable of killing *E. coli* and *Lactobacillus acidophilus* after aeration for 60–120 minutes in water. Wang et al., *Proceedings of the First International Conference on $TiO_2$ Photocatalytic Purification and Treatment of Water and Air* (London, Ontario, Canada, Nov. 8–13, 1992) pp. 733–39; Wang et al., *Proc. AWWA Conf*. (San Antonio, Tex., 1993); Savat et al., *J. Catalysis*, 127, 167–77 (1991) and Anderson et al., *Further Catalytic Purification of Water and Air*, 1, 405–20 (1993), report the gas phase detoxification of trichloroethylene (TCE) and other organic contaminants.

Co-pending and commonly owned U.S. patent application Ser. No. 08/647,070, filed May 9, 1996, discloses that the effectiveness of photocatalytic oxidation increases significantly when the relative humidity of the airstream is maintained at levels greater than about 40%. Under such conditions, it is possible to destroy the microorganisms in an airstream; however, the process requires a certain minimum residence time for complete effectiveness.

Electrostatic precipitators can trap microorganisms but cannot destroy them. Therefore, the hazard of such microorganisms remains. Specifically, electrostatic precipitators retain microorganisms on the grounded collection plate, which must be cleaned periodically to maintain the effectiveness of the precipitator at removing microorganisms from airstreains.

There remains a need for more efficient airstream disinfection devices.

SUMMARY OF THE INVENTION

This need is met by the present invention.

It has now been discovered that a synergistic effect is produced by combining electrostatic precipitation with photocatalytic oxidation. The electrostatic precipitation can be employed to remove microorganisms from the air and deposit them on a photocatalyst-coated surface illuminated by photons of an appropriate wavelength. The microorganisms are held captive electrostatically on the catalytic surface for a time greater than the minimum required residence time for photocatalytic destruction, and are completely destroyed and converted to $CO_2$ and $H_2O$.

Therefore, according to one aspect of the present invention, a method is provided for disinfecting an airstream containing microorganisms by electrostatic precipitation by passing the airstream through a space between at least one grounded collection plate, each collection plate having at least one electrode spaced apart therefrom connected to a source of electrical potential, wherein the improvement comprises contacting the airstream with a photocatalyst having a predetermined band gap energy coated on the surface of each grounded collection plate and illuminated with photons having a wavelength corresponding to the band gap energy of the photocatalyst, so that at least a portion of the microorganisms that collect on the grounded collection plate are destroyed by photocatalytic oxidation.

Preferred methods in accordance with the present invention maintain the relative humidity of the airstream between about 25% and about 75%. The preferred photocatalyst is $TiO_2$ having a band gap energy corresponding to UV light having a wavelength between about 300 and about 400 nm. With such a photocatalyst, UV photons having a wavelength between about 300 and 400 nm are preferably employed.

The present invention also includes devices embodying the inventive method. Thus, in accordance with another embodiment of the present invention, an electrostatic precipitator for disinfecting an airstream containing microorganisms is provided, having at least one grounded collection plate, each collection plate being spaced apart from at least one opposing electrode having a connector for connecting to a source of electrical potential, with each opposing collection plate-electrode combination being configured to permit the passage of the airstream therebetween, wherein the improvement comprises a coating on each grounded collection plate of a photocatalyst having a predetermined band gap energy, and a light source positioned to illuminate the photocatalyst coatings with photons having a wavelength corresponding to the band gap energy of the photocatalyst.

Preferred devices in accordance with the present invention include humidity controllers adapted to regulate the relative humidity of the airstream passing therethrough between about 25% and about 75%. Other preferred devices employ a UV light source between about 300 and about 400 nm and a $TiO_2$ photocatalyst having a band gap energy corresponding thereto.

The methods and devices of the present invention are adapted for use within HVAC systems of buildings or as stand-alone units. Thus, according to one aspect of this embodiment of the present invention, a device is provided for disinfecting air containing microorganisms having a duct through which the air is moved; a blower connected to the duct to move the air therethrough; at least one grounded collection plate coated with a photocatalyst having a predetermined band gap energy and disposed in the duct and spaced apart from at least one opposing electrode connected to a source of electrical potential to permit the passage of the air therethrough; and a light source disposed in sufficient proximity to each photocatalyst coating to illuminate the photocatalyst with photons having a wavelength corresponding to the band gap energy of the photocatalyst.

According to yet another aspect of this embodiment of the invention, a stand-alone device for disinfecting air containing microorganisms is provided having a chamber through which the air is moved; a blower connected to the chamber to move the air therethrough; at least one grounded collection plate coated with a photocatalyst having a predetermined band gap energy, each collection plate being spaced apart from at least one opposing electrode connected to a source of electrical potential to permit the passage of air therethrough; and a light source positioned to illuminate each photocatalyst coating with a source of photons having a wavelength corresponding to the band gap energy of the photocatalyst.

Preferred methods and devices in accordance with the present invention also coat the electrodes opposing the grounded collection plate with a photocatalyst having the same band gap energy as the photocatalyst coating the grounded collection plate.

The above and other objects, features and advantages of the present invention will become clear from the following description of the preferred embodiments considered in conjunction with the accompanying drawings.

It should be noted that the drawings are not necessarily to scale, but that certain elements have been expanded to show more clearly the various aspects of the present invention and their advantages.

DETAILED DESCRIPTION OF THE PREFERRED EMBODIMENT

Figure 3:
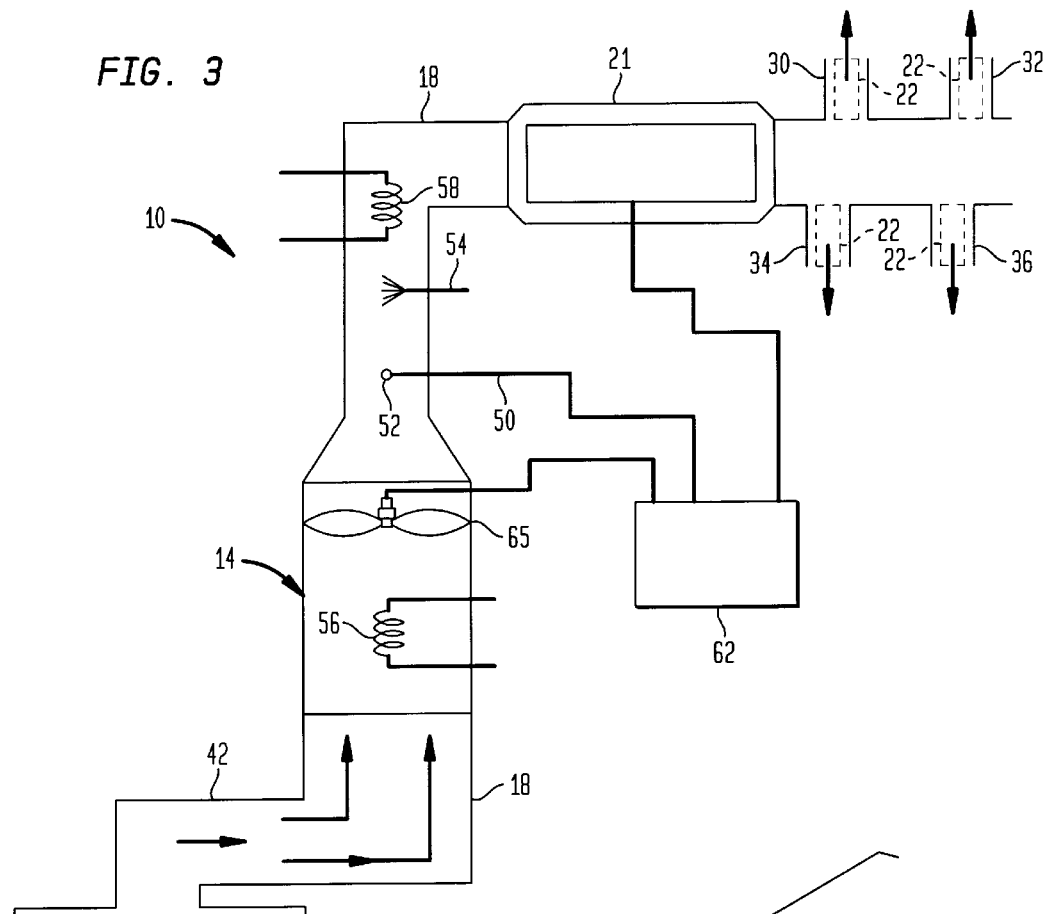
FIG. 3 depicts a HVAC system having a photocatalytic-electrostatic disinfection device of the present invention incorporated therein.

Referring now to the drawings wherein like elements are indicated by like numerals, an apparatus in accordance with the present invention embodying the method of the present invention is shown in FIG. 3 in which the numeral 10 depicts the system of this invention. In most buildings, a blower/fan causes the air from the various zones of an air-conditioned space to be drawn into a duct system via inlet openings and particle/aerosol filters 12. The air can then pass over the heating coil of the furnace or the heating/cooling coil of an air-conditioner/heat pump of the air-conditioning unit 14. The cooling coil will act as a dehumidifier because it condenses moisture from air as it cools the air.

The fan 65 of the air handling unit 14 will force the air passing over the coils 13 and 15 into a duct system 18. In FIG. 3 there is a master reactor 21 along the duct 18. In many installations this will be sufficient. However, in the embodiment of FIGS. 3 and 4, there is also shown a series of reactor units 22 disposed in branch lines of duct system 18.

Figure 4:
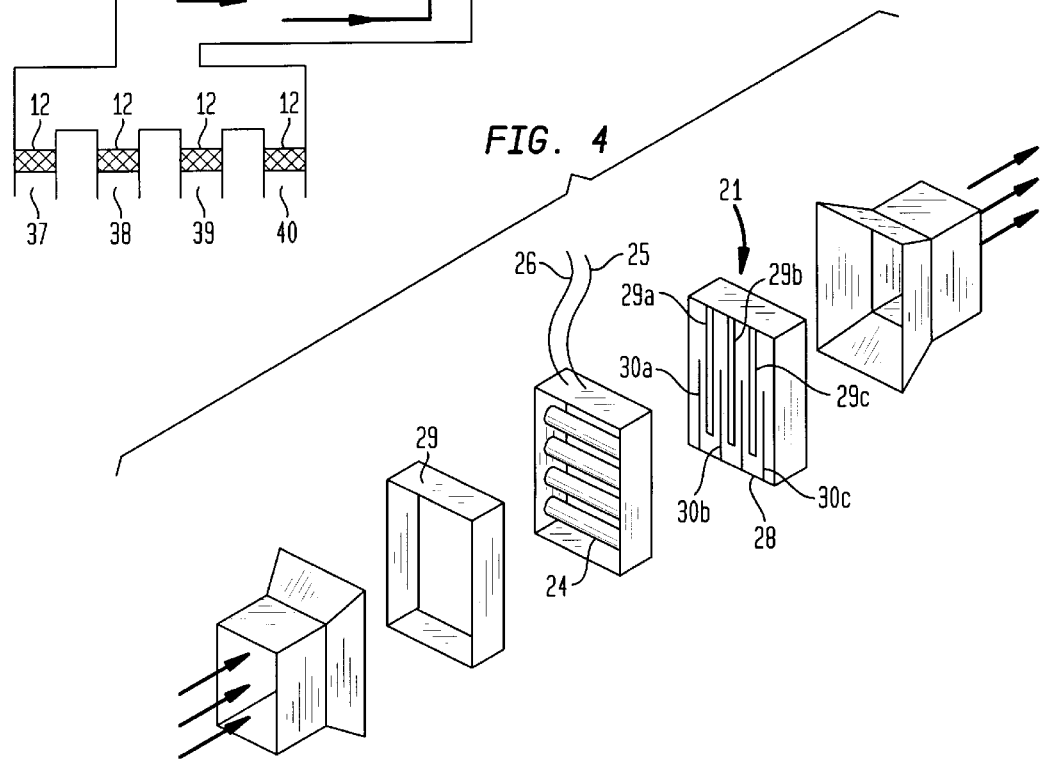
FIG. 4 is an exploded view illustrating a photocatalytic-electrostatic device according to the invention.
Figure 5:
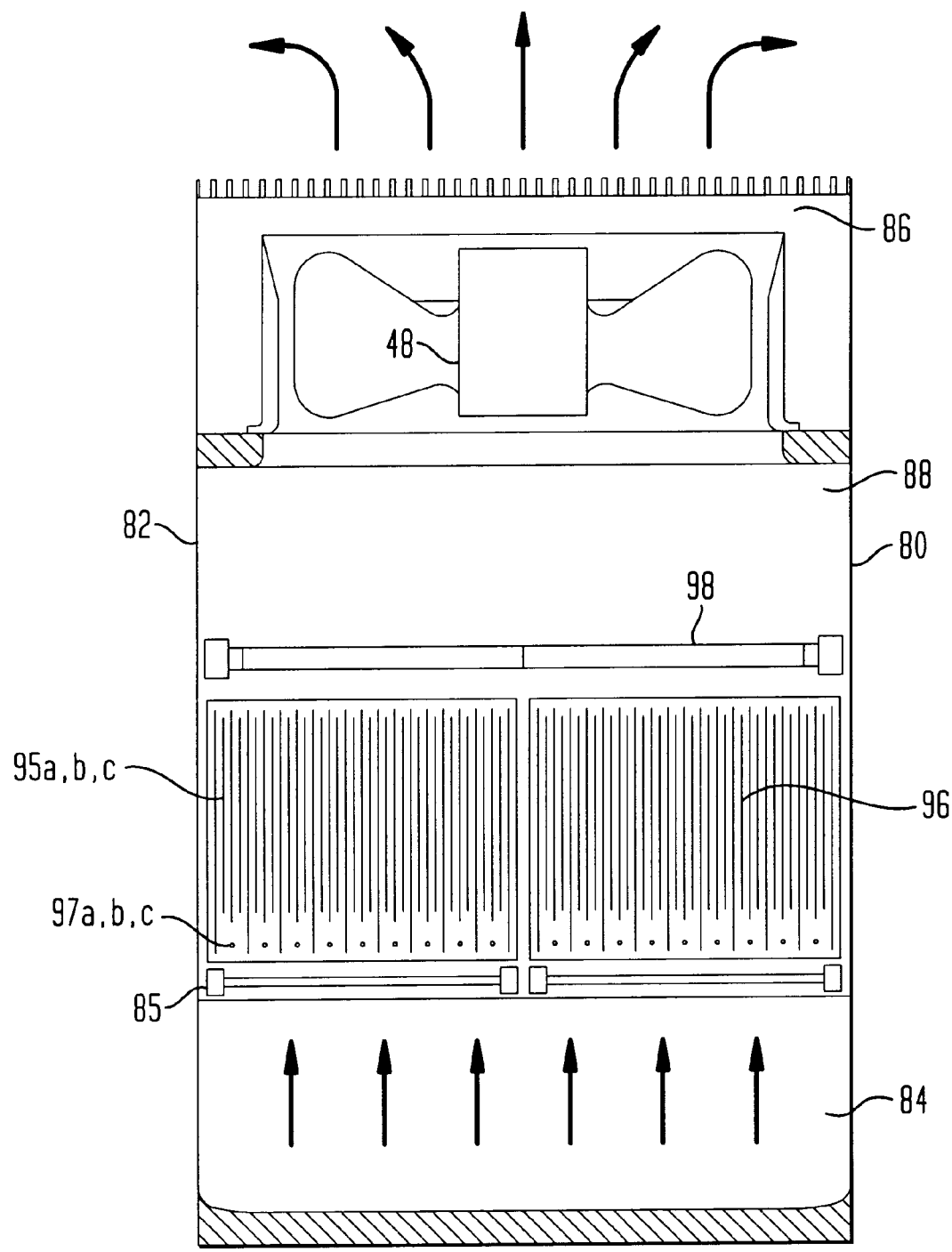
FIG. 5 is a longitudinal cross-sectional view of a stand-alone device according to the present invention.

FIG. 4 diagrammatically illustrates the major components within reactor 21. These components will also be found in reactors 22. The major components are catalyst-coated collection plates 29a, 29b, 29c, etc., spaced apart from electrodes 30a, 30b, 30c, etc., connected to a source of electrical potential (not shown), and a bank of UV lamps 24.

The lamps preferably deliver low energy photons of the UV-A and lower energy portion of the UV-B spectrum. A UV wavelength between about 300 and about 400 nm is preferred.

Essentially any material capable of catalyzing photocatalytic oxidation when illuminated with a source of photons is suitable for use as a photocatalyst in the present invention. Such materials are readily identified by those of ordinary skill in the art without undue experimentation. Examples of suitable photocatalysts are semiconductor materials such as $ZnO_2$, $TiO_2$, and the like; however, essentially any semiconductor material or a semiconductor doped with a noble metal or other metal such as silver may be employed. Preferably, the photocatalyst is used in combination with a source of photons including wavelengths corresponding to the band gap energy of the photocatalyst. A preferred source of photons is UV light. The preferred photocatalyst is $TiO_2$, which has a band gap energy falling within the energy range of UV photons of wavelengths 300–400 nm.

After passing through the reactors 22 and departing the branch conduits 30, 32, 34 and 36, the air is directed to room registers. In a large building there may be several dozen conduits of the 30–36 type branchings from a plurality of main ducts. Each room normally has an air return opening. The air is returned from each room and recirculated through the system via a series of ducts depicted by the numerals 37, 38, 39 and 40. These ducts contain filters 12 and merge into a collector duct 42 which returns the air to the intake side of the air-conditioning unit 14 where it may be re-cooled or re-heated and returned to the duct system 18.

The methods and devices of the present invention preferably maintain the relative humidity of the airstream passing therethrough within a range that is effective to enhance the catalytic effect of the photocatalyst. Preferably the relative humidity is maintained between about 25% and about 75%, and more preferably between about 40% and about 60%. A relative humidity of about 50% is most preferred.

Referring to FIG. 3, disposed along the length of duct 18 is a humidifier/dehumidifier unit 50 (sold by Sun Chemical as Model SUN13) with a detector probe of the type sold by Mamac as Model HV-2222, controlled by microprocessor 62. If detector 52 detects that the relative humidity in the air is less than 50%, a water spray or atomizer unit 54 is caused by microprocessor 62 to spray enough moisture into the airstream as a fine mist to raise the relative humidity to approximately 50%. If the relative humidity is over 75%, moisture is removed by a dehumidifier system here represented by cooling coil 56. Coil 56 can be a separate unit, but in many instances, the coils of unit 14 can be utilized. A separate backup coil 58 can also be provided. Dehumidification of air may be achieved by condensation of water using a cooling coil as shown in FIG. 3, or by other conventional techniques such as desiccant dehumidification.

Figure 1:
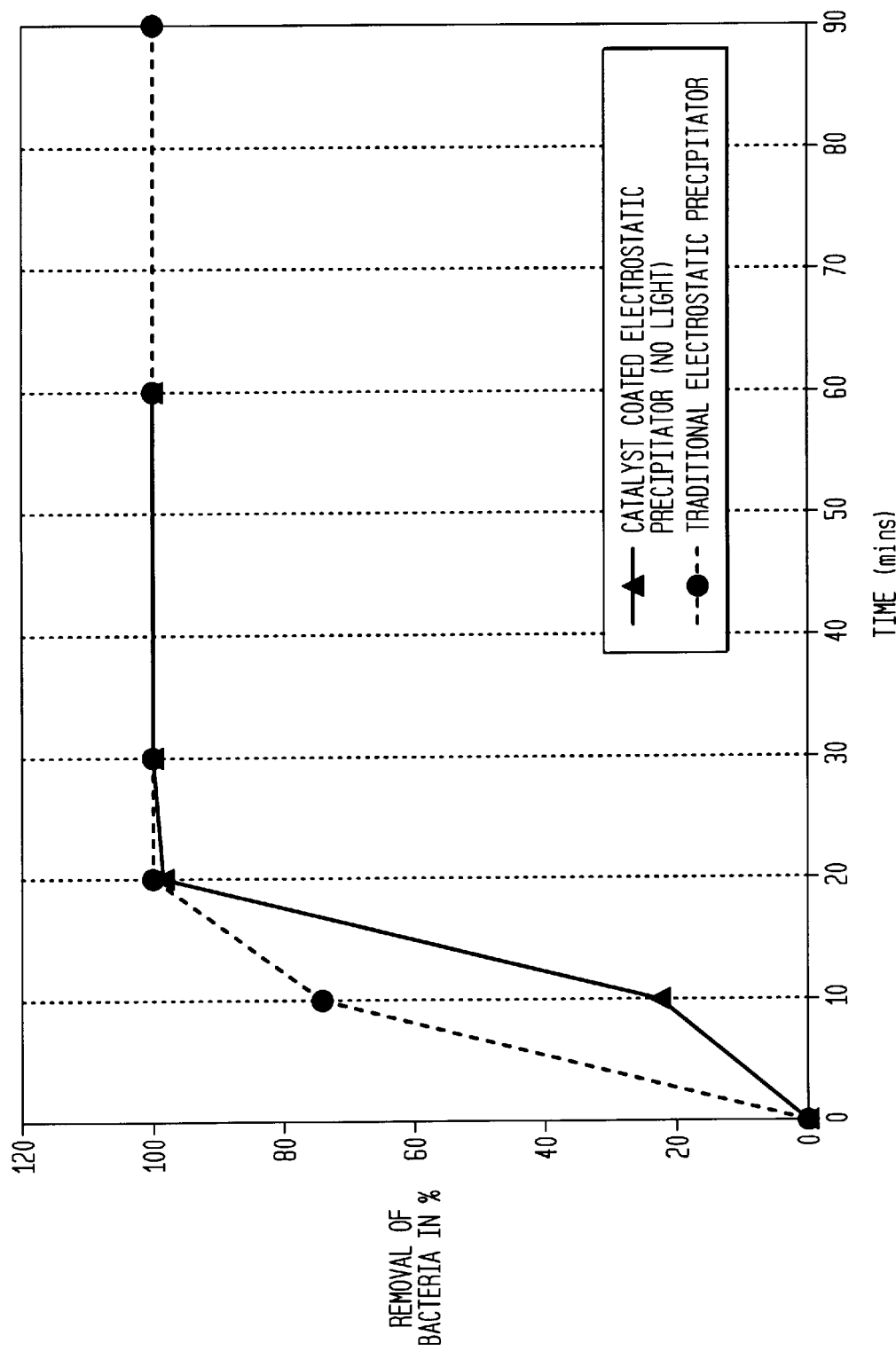
FIG. 1 depicts the efficiency of a prior art electrostatic precipitator and a precipitator having $TiO_2$-coated electrodes and collection plates, but without UV-illumination.
Figure 2:
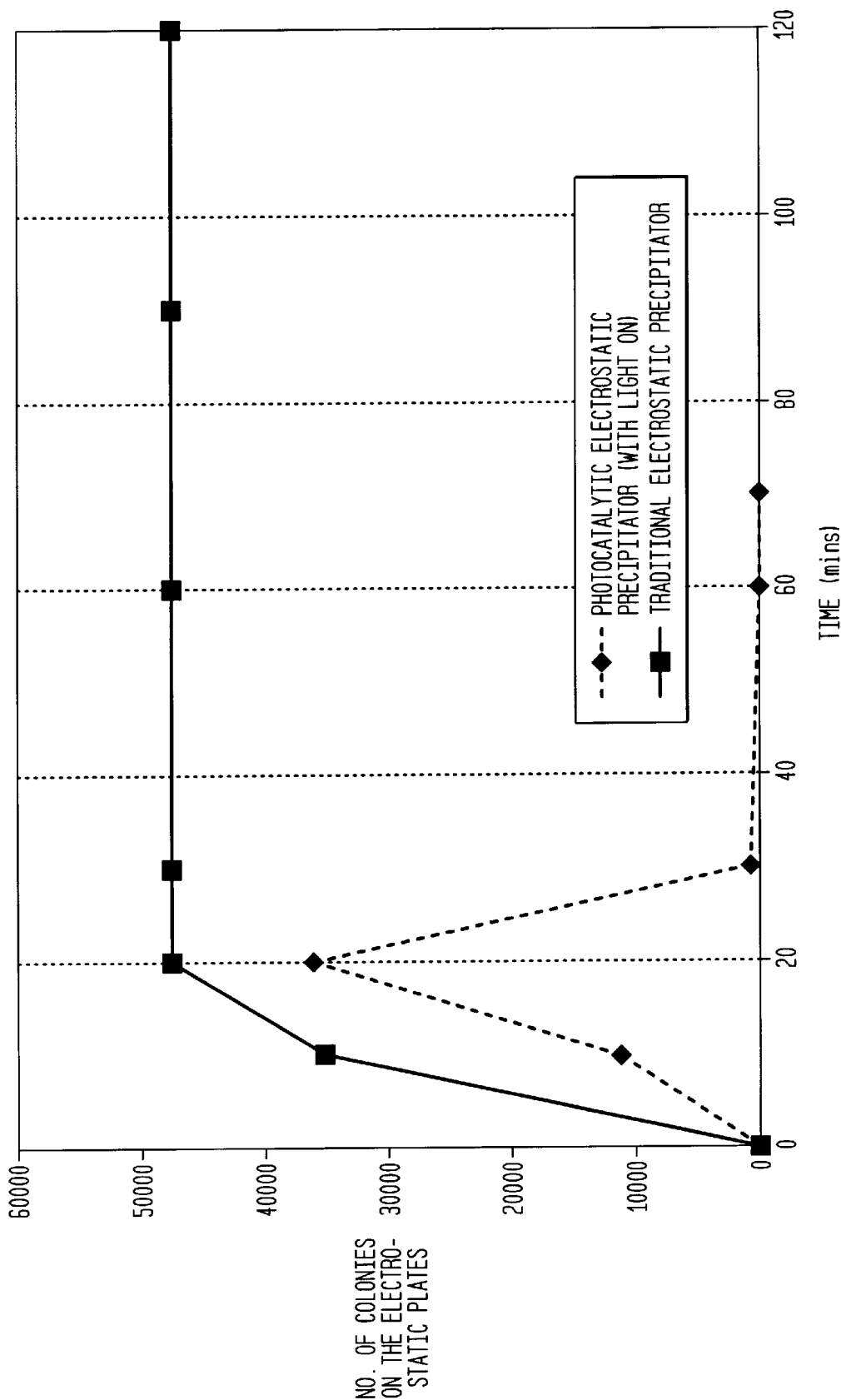
FIG. 2 depicts a comparison between the same prior art electrostatic precipitator and the same electrostatic precipitator with catalyst-coated collection plates and electrodes, but with UV-illumination of the catalyst coating.

The relative humidity is preferably selected so that complete destruction of the microorganisms that collect on the collection plate and opposing electrodes is achieved. For purposes of the present invention, destroyed microorganisms are defined as microorganisms that have been completely killed and catalytically decomposed, and does not include microorganisms that have been merely stunned, shocked or otherwise inactivated that are capable of being revived.

FIG. 3 discloses a master reactor 21 and branch reactors 22. In relatively small installations, only reactor 21 will be used. In relatively large installations, only reactors 22 will be used. They are combined in FIG. 3 to show that the combination can also be employed.

The reactors may be provided with their own independent relative humidity controls, so that each reactor functions as an independent device. Alternatively, each reactor may be adapted to the relative humidity controls of the HVAC system in which it is installed, thereby converting the HVAC system into an apparatus in accordance with the present invention. Under such circumstances, the reactor will consist essentially of an electrostatic precipitator having photocatalyst-coated grounded collection plates and opposing electrodes illuminated with a UV light source.

The reactors may also be installed in air supply registers of HVAC systems. As the air coies out of an HVAC duct, instead of going directly into a room, it is first treated by the photocatalytic-electrostatic disinfection method of the present invention. Single or multiple air outlets may be employed.

The essentials of this invention can be utilized independently of a duct system. Such a stand-alone unit 80 is shown in FIG. 5. The unit 80 includes a housing 82 having an inlet 84 and an outlet 86. Intermediate the inlet and outlet is a chamber 88 that includes a fan motor (not shown) for driving fan 48, and an electrostatic precipitator 96 upon which UV light is directed from a UV lamp 98.

Electrostatic precipitator 96 contains collection plates 95*a*, 95*b*, 95*c*, spaced apart from electrodes 97*a*, 97*b*, 97*c*, etc., connected to a source of electrical potential (not shown). The collection plates have photocatalyst coatings (not shown).

The unit 80 may be operated without its own humidity control system, or it may be operated in tandem with a humidifier or dehumidifier without departing from the method or devices of the present invention.

When power is supplied, the fan 48 will draw air into the inlet 84. A particulate prefilter 85 is provided to maintain the interior of the stand-alone unit free of large dirt particles. The prefilter may be omitted if the air is reasonably free of particulates. The UV light 98 is illuminated at the same time the fan begins to rotate.

The following example further illustrate the present invention, and is not to be construed as limiting the scope thereof. All parts and percentages are by weight unless expressly indicated to be otherwise, and all temperatures are in degrees Celsius.

EXAMPLE

MATERIALS AND METHODS

Bacteria Tested: *Serratia marcescens*.

Culture Preparation: A bacteria culture was prepared 24 hours prior to each run using a previously made culture and Trypticase Soy Broth (TSB). The TSB, which was used as a nutrient for the bacteria, was autoclaved before the culture was made to avoid any contamination. Using a sterilized inoculating loop, the bacteria was inoculated from the previously made culture and placed into a test tube containing TSB. The test tube was then placed in an incubator for 24 hours at 37° C.

Experimental Set-Up and Procedure: Experiments were conducted in an environmental chamber 4'×5'×6'. The chamber was sterilized over a period of 24 hours before the test. The test unit was placed in the chamber and bacteria was introduced through a nebulizer. A fan kept the air moving in the chamber to keep the bacteria airborne. The test unit was started and air samples were taken every 10 minutes using an Anderson Sampler. The plates from the samples were incubated for 24 hours. Bacterial colonies were counted using a colony counter.

A dark controlled experiment was conducted for each test. The conventional electrostatic precipitator unit and the new electrostatic photocatalytic unit were tested separately under the same conditions. The new photocatalytic unit was tested with and without UV lights turned on.

RESULTS

FIGS. 1 and 2 show the results. It is clear from FIG. 1 that both the conventional electrostatic filter and the combination electrostatic-photocatalytic filter are effective in removing bacteria from the airstream completely in 30 minutes or less. However, FIG. 2 shows that while bacteria that was precipitated on conventional electrostatic plates remained alive throughout the experiment, the bacteria on the UV-illuminated electrostatic-photocatalytic filter were almost completely destroyed in 30 minutes. After 60 minutes, the air in the chamber, as well as the electrostatic precipitator plates and electrodes, were completely sterilized.

The dark control conducted for the examples show a stable bacterial count for the duration of the experiment. Photocatalytic oxidation thus enhances the removal of microorganisms from the air by electrostatic precipitation.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications were intended to be included within the scope of the following claims.

What is claimed is:

1. A method for disinfecting an airstream containing microorganisms by electrostatic precipitation by passing the airstream through the space between at least one grounded collection plate having at least one electrode spaced apart therefrom connected to a source of electric potential, wherein the improvement comprises contacting the airstream with a photocatalyst having a predetermined band gap energy coated on the surface of each grounded collection plate and illuminated with photons having a wavelength corresponding to the band gap energy of the photocatalyst, so that at least a portion of the microorganisms that collect on the grounded collection plate are destroyed by photocatalytic oxidation.

2. The method of claim 1, wherein said at least one electrodes are also coated with said photocatalyst.

3. The method of claim 1, further including the step of adjusting the relative humidity of said airstream between about 25% and about 75% before the step of passing said airstream through said space between said at least one collection plate and said at least one electrode spaced apart therefrom.

4. The method of claim 3, wherein said relative humidity is adjusted between about 40% and about 60%.

5. The method of claim 4, wherein said relative humidity is adjusted to about 50%.

6. The method of claim 1, wherein said photocatalyst is a semiconductor.

7. The method of claim 6, wherein said semiconductor is doped with a noble metal or silver.

8. The method of claim 6, wherein said semiconductor is $TiO_2$.

9. The method of claim 8, wherein said source of photons comprises UV light having a wavelength from about 300 and about 400 nm.

10. The method of claim 1, wherein said source of photons comprises UV light.

11. An electrostatic precipitator for disinfecting an airstream containing microorganisms comprising at least one grounded collection plate, each collection plate being spaced apart from at least one opposing electrode having a connector for connecting to a source of electric potential, said opposing collection plate-electrode combination being configured to permit the passage of the airstream therebetween, wherein the improvement comprises a coating on each grounded collection plate of a photocatalyst having predetermined band gap energy and a light source positioned to illuminate each photocatalyst coating with photons having a wavelength corresponding to the band gap energy of the photocatalyst.

12. The electrostatic precipitator of claim 11, wherein said at least one electrode is coated with a photocatalyst having a band gap energy equivalent to the band gap energy of the photocatalyst coated on said at least one collection plate.

13. The electrostatic precipitator of claim 11, wherein said photocatalyst is a semiconductor.

14. The electrostatic precipitator of claim 13, wherein said semiconductor is doped with a noble metal or silver.

15. The electrostatic precipitator of claim 13, wherein said semiconductor is $TiO_2$.

16. The electrostatic precipitator of claim 15, wherein said photons have a wavelength between about 300 and about 400 nm.

17. The electrostatic precipitator of claim 11, wherein said photons have a UV wavelength.

18. The electrostatic precipitator of claim 11, further including a humidity controller adapted to regulate the relative humidity of said airstream.

19. A stand-alone device for disinfecting air containing microorganisms comprising:
    a chamber through which said air is moved;
    a blower connected to said chamber to move said air therethrough;
    the electrostatic precipitator of claim 11, disposed in said chamber so that said air is moved therethrough.

20. The device of claim 19, further including a humidity controller adapted to maintain the relative humidity of the air in said chamber.

21. The stand-alone device of claim 19, wherein said photocatalyst is a semiconductor.

22. A device for disinfecting air containing microorganisms comprising the electrostatic precipitator of claim 11 disposed in an air supply register of a heating, ventilating and air conditioning system, wherein said heating, ventilating and air conditioning system has a blower to move air through said air supply register.

* * * * *

UNITED STATES PATENT AND TRADEMARK OFFICE
CERTIFICATE OF CORRECTION

PATENT NO. : 5,993,738
DATED : November 30, 1999
INVENTOR(S) : Goswami

It is certified that error appears in the above-identified patent and that said Letters Patent is hereby corrected as shown below:

On the title page, item [75]:

Inventor "Goswani" should read -- Goswami --.

Column 6, line 4, "coies" should read -- comes --.
Column 7, line 38, "electrodes are" should read -- electrode is --.

Signed and Sealed this

Twenty-sixth Day of December, 2000

Attest:

Q. TODD DICKINSON

Attesting Officer

Director of Patents and Trademarks